United States Patent [19]

Eguchi et al.

[11] Patent Number: 4,578,563
[45] Date of Patent: Mar. 25, 1986

[54] STEAM GENERATOR

[75] Inventors: Kenzo Eguchi; Jiro Kobayashi, both of Tokyo, Japan

[73] Assignees: Taishin Electric Ind. Co., Ltd.; Toshiba Medical Supply Co., Ltd., both of Tokyo, Japan

[21] Appl. No.: 660,509

[22] Filed: Oct. 12, 1984

[30] Foreign Application Priority Data

Oct. 25, 1983 [JP] Japan ............................ 58-163956[U]
Oct. 25, 1983 [JP] Japan ............................ 58-163957[U]
Oct. 25, 1983 [JP] Japan ............................ 58-163958[U]
Oct. 25, 1983 [JP] Japan ............................ 58-163959[U]

[51] Int. Cl.4 ............................................ F22B 27/00
[52] U.S. Cl. ................................... 219/273; 219/275
[58] Field of Search ............... 219/271, 272, 273, 274, 219/275, 276, 362; 126/113; 261/4, 5, 142, DIG. 65; 122/4 A, 13 A, 27, 28

[56] References Cited

U.S. PATENT DOCUMENTS

| | | | |
|---|---|---|---|
| 1,939,783 | 12/1933 | Knowles | 219/272 |
| 2,002,294 | 5/1935 | McMath | 126/113 |
| 2,365,243 | 12/1944 | Boren | 219/362 |
| 3,406,097 | 10/1968 | Port | 219/275 |
| 3,721,802 | 3/1973 | Chrisman | 219/273 |
| 4,346,048 | 8/1982 | Gates | 261/142 |
| 4,366,051 | 12/1982 | Fischel | 422/26 |

FOREIGN PATENT DOCUMENTS

| | | | |
|---|---|---|---|
| 1026491 | 3/1958 | Fed. Rep. of Germany | 219/273 |
| 2514771 | 9/1976 | Fed. Rep. of Germany | 219/273 |

Primary Examiner—C. L. Albritton
Assistant Examiner—Teresa J. Walberg
Attorney, Agent, or Firm—Burgess, Ryan & Wayne

[57] ABSTRACT

A steam generator is proposed to spray steam in a beauty shop, a barbershop or the like. In the steam generator, a small amount of water is continuously supplied to a heated vapor assembly and is instantaneously converted to steam. A preparation time can be greatly shortened after the vapor assembly is heated. Thereafter, steam can be stably and continuously supplied. Discharge electrodes are arranged in a steam tube extending from the vapor assembly to effectively ionize the steam.

6 Claims, 9 Drawing Figures

FIG. IA
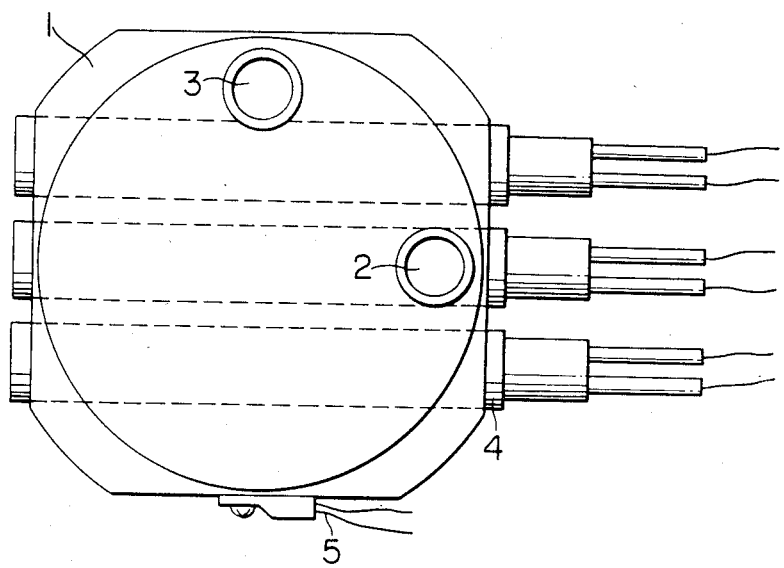
FIG. IB
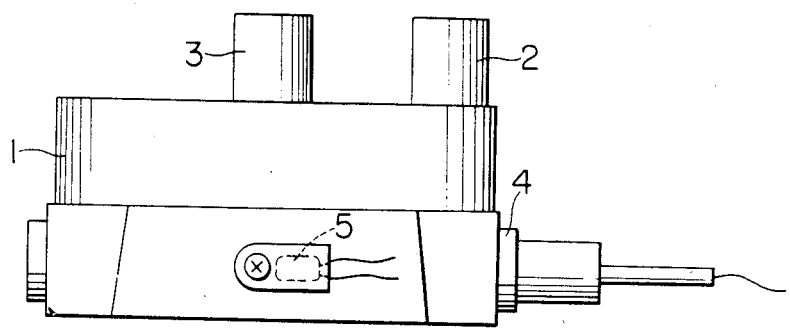

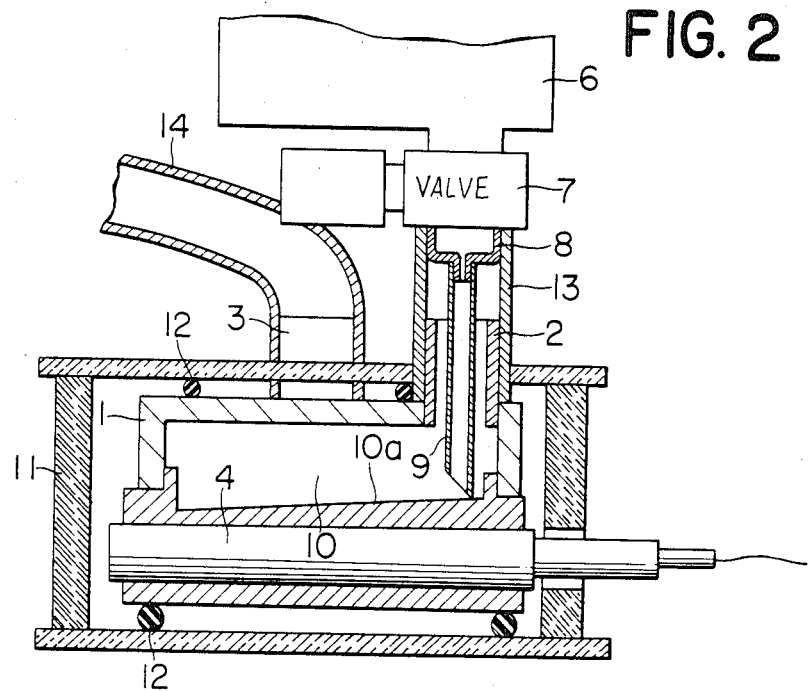
FIG. 2
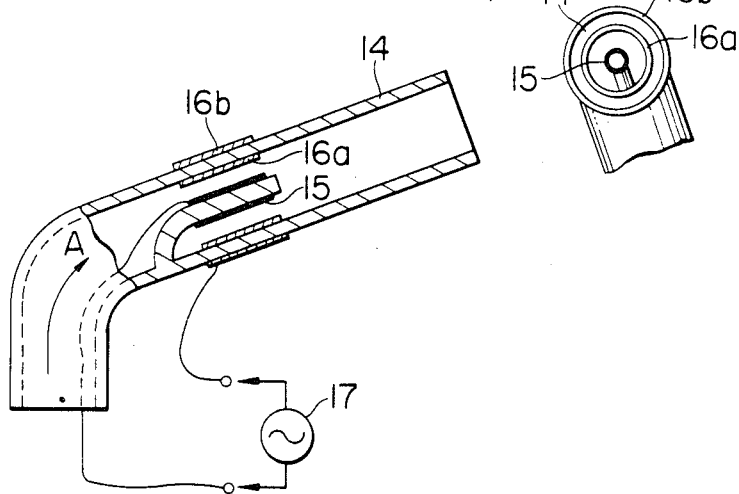
FIG. 3A (PRIOR ART)
FIG. 3B

STEAM GENERATOR

BACKGROUND OF THE INVENTION

I. Field of the Invention

The present invention relates to a steam generator for spraying steam to a face in a beauty shop, a barbershop or the like.

II. Description of the Prior Art

Vacuum suction and brushing have been recently performed in a beauty shop or the like while steam is being sprayed to the face. In a barbershop or the like, steam is sprayed on a face to give proper humidity and temperature so as to shave. In particular, a sterilization effect is obtained when ionized steam is sprayed on the face. In addition, circulation of blood is facilitated, and the metabolism is activated.

Conventionally, water in a container is heated by a heater to boil to obtain steam for the above purposes. It takes about 30 minutes or longer to obtain steam after water is heated.

SUMMARY OF THE INVENTION

It is a first object of the present invention to provide a steam generator which requires a very short preparation period and which can continuously and stably generate steam.

It is a second object of the present invention to provide a discharge electrode structure for effectively ionizing the generated steam.

It is a third object of the present invention to provide a simple steam generator which can be easily handled and maintained by an unskilled person who is not accustomed to mechanical operation.

In order to achieve the above objects of the present invention, a small amount of water is continuously supplied to a vapor chamber in a heated vapor assembly, thereby sequentially evaporating water. Since the construction of the vapor assembly is compact, it takes only about one minute until the vapor chamber is heated to a necessary temperature for instantaneously generating steam. The preparation time can be greatly decreased. A pair of rod-like electrodes horizontally extend through the opposing walls of a steam pipe, respectively, and oppose each other inside the steam pipe. A discharge occurs between the rod-like electrodes to ionize and activate steam.

Other objects, features and advantages of the present invention will be apparent from the detailed description in conjunction with the following accompanying drawings.

BRIEF DESCRIPTION OF THE DRAWINGS

FIG. 1A is a plan view of a vapor assembly in a steam generator according to a first embodiment of the present invention, and FIG. 1B is a side view of the vapor assembly shown in FIG. 1A;

FIG. 2 is a sectional view of a steam generator using the vapor assembly shown in FIG. 1A;

FIGS. 3A and 3B respectively show a conventional discharge electrode structure for ionization;

Figure 4:
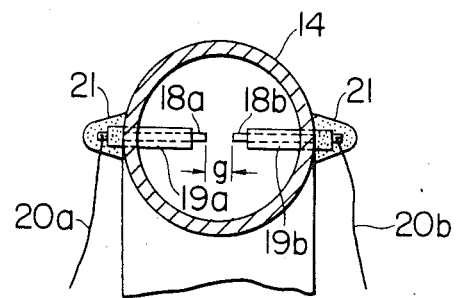
FIG. 4 is a sectional view showing a discharge electrode structure of the steam generator according to the first embodiment.

DETAILED DESCRIPTION OF THE PREFERRED EMBODIMENTS:

FIGS. 1A, 1B and 2 show a first embodiment of the present invention. Referring to FIGS. 1A and 1B, reference numeral 1 denotes a vapor assembly made of a heat-conductive metal. The vapor assembly 1 has a vapor chamber, an inlet port 2 for receiving water in the vapor chamber, and a drain port 3 for discharging steam. A plurality of holes (three holes in this embodiment) are formed in the lower portion of the vapor assembly to mount pipe heaters 4. Reference numeral 5 denotes a temperature control thermistor mounted on the side wall of the vapor assembly 1.

Referring to FIG. 2, reference numeral 6 denotes a water tank; 7, an electromagnetic valve; and 8, a water supply port having a distal end with an aperture. This aperture has a diameter of 0.6 mm. Reference numeral 9 denotes a small water tube extending from the water supply port 8 to a bottom surface 10a of a vapor chamber 10 of the vapor assembly 1. The small water tube 9 comprises a heat-resistant silicone tube having an inner diameter of 2 mm. The small water tube 9 may comprise a metal tube such as a brass tube. The bottom surface 10a of the vapor chamber 10 is inclined from one end to the other end thereof so as to cause water flow along its inclination. An upper unit having the water inlet port 2 and the steam drain port 3 is manufactured separately from a lower unit having the heaters 4 and is pressed thereon to constitute the vapor assembly 1. The vapor assembly 1 is made of nickel-plated brass.

Reference numeral 11 denotes a heat-insulating cover to surround the vapor assembly 1 and the heaters 4. The heat-insulating cover 11 consists of a cylinder and upper and lower plates made of an epoxy resin. The cover 11 may be made of asbestos, glass fiber or the like. Reference numerals 12 denote O-rings made of heat-resistant rubber. The O-rings 12 cause the vapor assembly 1 to float with respect to the cover 11. Reference numeral 13 denotes a tube for connecting the water supply port 8 and the inlet port 2. Reference numeral 14 denotes a steam tube for connecting the drain port 3 and a steam spray nozzle (not shown). Discharge electrodes to be described later are mounted in the steam tube 14 to ionize the steam.

When the heaters 4 are energized to generate steam, the vapor assembly 1 is heated to a temperature of 180° C. within about one minute. The thermistor 5 detects this temperature and generates a signal. The electromagnetic valve 7 is energized in response to this signal, so that water is supplied from the water supply port 8. In this case, since the aperture of the water supply port 8 is as small as 0.6 mm, a small amount of water is continuously supplied to the bottom 10a of the vapor chamber 10 through the small water tube 9. Water reaching the bottom surface 10a flows along the inclination since the bottom surface 10a is inclined. During this flow, the water is heated by the vapor assembly 1 and is converted to steam. The steam is discharged from the drain port 3 and is ionized in the steam tube 14 and is then sprayed from the spray nozzle (not shown). The steam can be sprayed and reach to a distance of about 60 cm due to the vapor pressure although the distance varies in accordance with the nozzle diameter. The vapor assembly 1 is kept heated at a temperature of 180°±20° C.

When the small water tube 9 is not provided, water from the water supply pipe 8 becomes droplets. The droplets intermittently drip on the bottom surface 10a of the vapor chamber. If this occurs, the steam sprayed from the nozzle also becomes intermittent, as if "breathing" occurs, resulting in inconvenience. According to the first embodiment, the small water tube 9 is provided in such a manner that the distal end thereof is in contact with the surface of the bottom surface 10a. Therefore, the flow of supplied water is continuous and the steam is continuously sprayed. However, the distal end of the small water tube 9 need not be in contact with the bottom surface 10a and can be disposed in the vicinity of the bottom surface 10a. In this case, water is bridged between the distal end of the small water tube 9 and the bottom surface 10a due to the surface tension of water, thereby obtaining a continuous water flow.

Since the bottom surface 10a of the vapor chamber 10 is inclined to cause water to flow from one end to the other end thereof, water can be effectively heated and converted to steam. When the bottom surface comprises a flat surface, water will not flow and collects at the water inlet zone, thus greatly degrading the vapor efficiency. According to the first embodiment, the bottom surface 10a is inclined. However, the vapor assembly 1 itself may instead be slightly inclined.

The drain port 3 is formed at either the right or left side of the center of inclination of the bottom surface 10a. When the drain port is at a position immediately above a water flow along the bottom surface, large steam particles are discharged from the drain port and are sprayed from the nozzle. However, according to the above embodiment, fine steam particles can be constantly discharged from the drain port, thereby obtaining suitable steam for the desired purpose.

In the above embodiment, the vapor assembly 1 is made of nickel-plated brass. At least the vapor chamber 10 and the drain port must be plated with nickel. Even if nickel plating is not carried out, appropriate vapor function is possible. However, the resultant vapor has a metallic smell and cannot be used for the purposes of the present invention. When stainless steel is used in place of brass, no odor occurs, but stainless steel has a poor heat conductivity. Temperature varies in the respective parts of the vapor assembly, and the vapor efficiency is degraded. Simultaneously, the vapor pressure is decreased to shorten the spray distance of the steam emitted from the nozzle.

Discharge electrodes are arranged in midway along the steam tube 14 to ionize the steam. Ionized steam is obtained by discharging the steam. Prior to ionization the steam is relatively transparent, however, when ionized, the steam particles become very fine, so that the ionized steam looks whitish.

The conventional discharge electrodes for ionizing the steam are arranged in a manner shown in FIGS. 3A and 3B. Referring to FIGS. 3A and 3B, reference numeral 14 denotes a steam tube which comprises, for example, a glass tube. The steam generated by the vapor assembly flows in a direction indicated by arrow A. Reference numeral 15 denotes an electrode arranged along the central axis of the steam tube 14. The electrode 15 comprises a copper tube mounted on a glass support extending inside the tube 14. Reference numerals 16a and 16b denote electrodes each of which is made of nickel silver. The electrodes 16a and 16b are respectively mounted on the inner and outer surfaces of the tube 14 so as to oppose each other. The electrodes 16a and 16b and the glass wall constitute a capacitor. When a power source 17 is connected to apply a high voltage between the electrodes 15 and 16b, a discharge occurs between the electrodes 15 and 16a, so that electrons are bombarded against the steam particles flowing inside the tube, with the result that the steam is ionized and activated.

However, in the case of the conventional discharge electrode assembly, a high voltage is required. In addition to this disadvantage, in an operational test wherein a cycle of a discharge time of one hour and a nondischarge time of one hour is repeated, the discharge operation is disabled after an actual discharge time of about 4 hours. This is because the opposing area between the electrodes 15 and 16a is large and an arc discharge tends to occur at specific positions between the electrodes. These positions become worn, and oxide film is formed or a fur is deposited thereon. Thus, the discharge function is disabled.

According to the present invention, there is provided a simple electrode structure which requires only a low application voltage and provides a long time period of discharge operation.

FIG. 4 shows a typical discharge electrode structure. Reference numerals 18a and 18b denote a pair of rod-like electrodes horizontally extending through the opposing walls of the steam tube 14, respectively. The electrodes 18a and 18b oppose each other and are spaced by a predetermined gap g from each other. Only the distal end portions of the electrodes 18a and 18b are exposed. The remaining portions of the electrodes 18a and 18b are covered with insulating tubes 19a and 19b, respectively. The ends of the electrodes 18a and 18b which are opposite to the exposed end portions are respectively connected to lead wires 20a and 20b connected to a high voltage source and are fixed by a silicone resin 21 on the outer surface of the steam tube 14.

In this embodiment, the steam tube 14 was comprised of a glass tube having an inner diameter of 12.5 mm, and the gap g was 1.5 mm. Each of the electrodes 18a and 18b comprised an Au alloy rod having a diameter of 0.6 mm. The insulating tubes 19a and 19b were made of Teflon.

In this configuration of the discharge electrode assembly, in an operational test wherein a cycle of a discharge time of one hour at a voltage of 15 kV and a nondischarge time of one hour was repeated, the cycle could be repeated for an actual discharge time of more than several thousands of hours.

When portions of the electrodes 18a and 18b except for the distal ends thereof are not covered with the insulating tubes 19a and 19b, respectively, a surface discharge occurs from the proximal ends of the electrodes along the inner surface of the steam tube 14. This discharge does not contribute to ionization of the steam. Each insulating tube serves to elongate a surface discharge distance and to cause normal discharge between exposed distal end portions of the electrodes, thereby providing effective ionization of steam. Even if the oxide film and fur are formed on the exposed portions of the electrodes 18a and 18b, these are removed by the discharge function and the electrodes 18a and 18b are kept clean. The pair of electrodes 18a and 18b must be horizontally aligned. If the electrodes are aligned vertically or obliquely, water droplets attach to the distal end of the upper electrode, thereby preventing discharge.

A passing hole (to be referred to as an aperture) must be formed at a part of the water supply portion so as to continuously supply water in correspondence with the vapor rate of the vapor assembly. In the embodiment shown in FIG. 2, the hole having the diameter of 0.6 mm and formed at the distal end of the water supply port 8 corresponds to the aperture. In general, fine dust is unavoidably mixed in water. When the steam generator is used for a given period, dust clogs the aperture preventing a smooth flow of water. As a result, a predetermined amount of water cannot be supplied. For this reason, dust must be removed.

Figure 5:
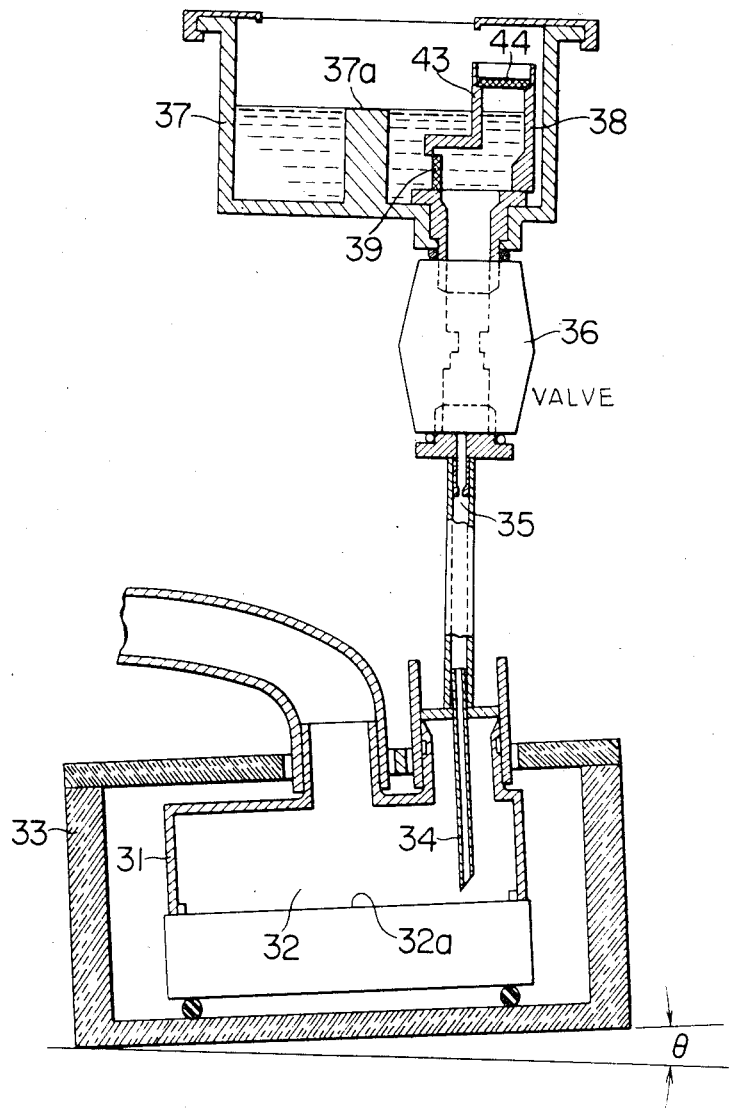
FIG. 5 is a sectional view of a steam generator according to a second embodiment of the present invention.

FIG. 5 shows a steam generator with a dust remover according to a second embodiment of the present invention. Referring to FIG. 5, reference numeral 31 denotes a vapor assembly having a vapor chamber 32 therein. Reference numeral 33 denotes a heat-insulating cover for surrounding the vapor assembly 31. The vapor assembly 31 is inclined by an angle θ, for example, 5° in this embodiment, so as to incline a bottom surface 32a of the vapor chamber 32. Reference numeral 34 denotes a small water tube made of a brass pipe; 35, an aperture; 36, an electromagnetic valve; and 37, a tank support for supporting a water tank. A water tank cartridge is disposed upside down in the tank support 37, and a cover of the water tank is pushed up by a projection 37a so as to balance between water in the tank and the atmospheric pressure. In this manner, the water level in the tank support 37 is controlled in the vicinity of the distal end of the projection 37a.

Figure 7:
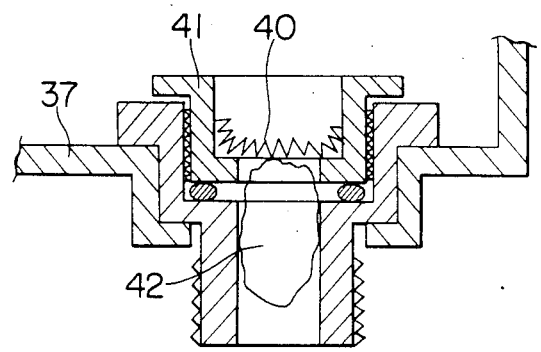
FIG. 7 is a sectional view of a dust remover made on an experimental basis.

Reference numeral 38 denotes a dust remover disposed in the tank support 37 to remove dust from water. The dust is removed by a metal net 39, and dust-free water is supplied to the vapor chamber 32 through the aperture 35. As shown in FIG. 7, when a dust remover 41 having a metal net 40 is arranged to cover the water inlet port of the tank support 37 which is connected to the electromagnetic valve, a bubble 42 flowing from the vapor chamber through the aperture is left under the metal net 40 without passing therethrough. As a result, any further water supply is disabled, resulting in inconvenience. Therefore, in the embodiment shown in FIG. 5, a projection 43 with an upper opening is provided to remove the bubbles, and a second metal net 44 is provided above the water level to prevent dust from entering the water.

According to this embodiment, water filtered through the metal net 39 is free from dust, and therefore dust does not clog the aperture 35. In addition, the reversely flowing bubble can be easily removed, so that the water flow will not be stopped. Thus, a predetermined amount of water can be stably and continuously supplied to the vapor chamber.

It is very important to constantly supply a predetermined amount of water to the vapor chamber so as to obtain a predetermined volume of steam. For this reason, the aperture for determining the amount of water supplied to the vapor chamber must always have a predetermined diameter. Although the water is filtered by the dust remover, the diameter of the aperture changes due to buildup of sediment when a certain period of time has elapsed. The aperture must be properly maintained and cleaned. In the first and second embodiments, the steam generator must be disassembled to clean the aperture portion. The disassembly cannot be easily performed by an unskilled person who is not accustomed to mechanical operation.

Figure 6:
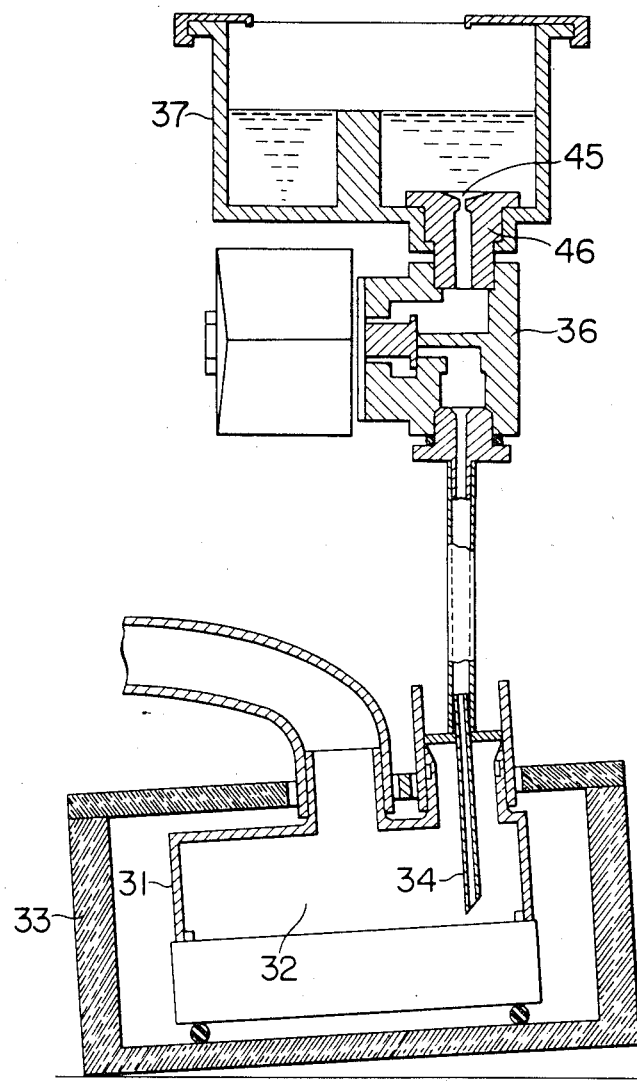
FIG. 6 is a sectional view of a steam generator according to a third embodiment of the present invention.

FIG. 6 shows a steam generator which can be easily maintained and cleaned according to a third embodiment of the present invention. The steam generator in FIG. 6 is substantially the same as that in FIG. 5, except that an aperture 45 is formed in a coupling 46 for coupling a tank support 37 and an electromagnetic valve 36. In this case, a dust remover is not used. According to the third embodiment, when a diameter of the aperture 45 changes due to dust mixed in water, a thin pin is inserted from the opening of the tank support 37 to extend through the aperture 45. Thus, easy maintenance and cleaning can be performed. In this case, a bubble flowing in the reverse direction is stopped under the aperture 45 and will not float through the aperture 34 since the pressure of the vapor chamber is balanced with the water pressure in the tank support. In order to prevent this, the electromagnetic valve 36 is instantaneously operated once or twice every minute. The bubble stopped under the aperture 45 can float due to the pressure exerted upon it by the opening/closing operation of the electromagnetic valve. The bubble located under the electromagnetic valve is moved to the vapor chamber 32. The operation of the electromagnetic valve can be easily automated by an electrical circuit.

According to this embodiment, the generator can be easily maintained and cleaned by an unskilled person to constantly obtain a predetermined volume of steam.

According to the present invention as described above, a small amount of water is continuously supplied to the vapor chamber, and the water is sequentially vaporized, so that the preparation time can be greatly shortened. In particular, when water is supplied through the small water tube from the valve of the water supply arrangement to the bottom surface of the vapor chamber, a continuous flow is obtained. As a result, stable and uniform steam spraying from the nozzle can be achieved. The discharge electrode structure is simple and provides a stable discharge for a long period of time. In addition, a voltage applied to the electrodes can be decreased.

What is claimed is:

1. A steam generator comprising:
   water supply means for continuously supplying a small amount of water;
   a vapor assembly having an inlet port for receiving water from said water supply means, a heat-conductive vapor chamber for sequentially heating and vaporizing water from said water supply means, and a drain port for discharging steam;
   a heater for heating said vapor assembly, and a heat-insulating cover for surrounding said vapor assembly and said heater; and
   said water supply means including a dust remover, arranged in a tank support for mounting a cartridge type water tank, for filtering water supplied to said vapor chamber, said dust remover being provided with a filtering material for filtering water at a side surface thereof immersed in water in said tank support, and a projection opening to remove a bubble reversely flowing from said vapor chamber.

2. A steam generator comprising:
   water supply means for continuously supplying a small amount of water;
   a vapor assembly having an inlet portion for receiving water from said water supply means, a heat-conductive vapor chamber for sequentially heating and vaporizing water from said water supply means, and a drain port for discharging steam;

a heater for heating said vapor assembly;

a heat-insulating cover for surrounding said vapor assembly and said heater;

said water supply means including a small water tube extending from a valve for controlling the supply of water from a water tank, a distal end of said small water tube being one of located in contact with a bottom surface of said vapor chamber and located in a vicinity of said bottom surface; and said bottom surface being inclined such that water supplied to one end thereof flows to the other end thereof.

3. A steam generator according to claim 2, wherein said water supply means has an aperture, having a predetermined diameter, for determining a proper amount of water to be supplied, said aperture being an aperture formed in a coupling between a tank support for mounting a cartridge water tank and a valve for controlling the supply of water.

4. A steam generator according to claim 2, wherein said vapor assembly is made of brass, and at least said vapor chamber and said drain port are plated with nickel.

5. A steam generator comprising:

water supply means for continuously supplying a small amount of water;

a vapor assembly having an inlet port for receiving water from said water supply means, a heat-conductive vapor chamber for sequentially heating and vaporizing water from said water supply means, and a drain port for discharging steam;

a heater for heating said vapor assembly;

a heat-insulating cover for surrounding said vapor assembly and said heater;

discharge electrode means, arranged in a steam tube connected to said drain port, for ionizing the steam;

wherein said water supply means including a small water tube extending from a valve for controlling the supply of water from a water tank, a distal end of said small water tube being one of located in contact with a bottom surface of said vapor chamber and being located in a vicinity of said bottom surface; and said bottom surface being inclined such that water supplied to one end thereof flows to the other end thereof.

6. A steam generator comprising:

water supply means for continuously supplying a small amount of water;

a vapor assembly having an inlet port for receiving water from said water supply means, a heat-conductive vapor chamber for sequentially heating and vaporizing water from said water supply means, and a drain port for discharging steam;

a heater for heating said vapor assembly;

a heat-insulating cover for surrounding said vapor assembly and said heater;

discharge electrode means, arranged in a steam tube connected to said drain port, for ionizing the steam, said discharge electrode means including a pair of rod electrodes, distal ends of which are exposed and remaining portions of which are respectively covered with insulating tubes, said rod electrodes horizontally extending through opposing tube walls of said steam tube, respectively, and said rod electrodes opposing each other with a predetermined gap defined therebetween, whereby a high voltage is applied between said pair of rod electrodes to ionize the steam.

* * * * *